United States Patent [19]

Runge et al.

[11] Patent Number: 5,823,930
[45] Date of Patent: Oct. 20, 1998

[54] CAM CONTROLLED PULSATILE FLOW PUMP FOR NEONATAL AND BIVENTRICULAR CARDIAC SUPPORT SYSTEMS

[76] Inventors: Thomas M. Runge, P.O. Box 50045, Austin, Tex. 78763; Fred O. Bohls, 2103 Meadowbrook, Austin, Tex. 78703

[21] Appl. No.: 600,686

[22] Filed: Feb. 13, 1996

[51] Int. Cl.⁶ .................................................. A61M 1/10
[52] U.S. Cl. ............................................... 600/16; 623/3
[58] Field of Search ........................ 128/DIG. 3; 600/16, 600/17, 18; 623/3, 26; 417/478, 479, 480, 510

[56] References Cited

U.S. PATENT DOCUMENTS

| | | | |
|---|---|---|---|
| 2,917,751 | 12/1959 | Fry et al. .................................... | 523/3 |
| 3,518,033 | 6/1970 | Anderson ................................. | 417/478 |
| 4,143,425 | 3/1979 | Runge . | |
| 4,293,961 | 10/1981 | Runge ......................................... | 623/3 |
| 5,383,839 | 1/1995 | Bohls ........................................ | 600/16 |

*Primary Examiner*—William F. Kamm
*Assistant Examiner*—George R. Evanisko
*Attorney, Agent, or Firm*—Brady, O'Boyle & Gates

[57] ABSTRACT

A cam controlled pulsatile flow pump for neonatal and biventricular cardiac support systems wherein cylindrical cams having various profiles designed for a particular patient are selectively mounted on the output shaft of a motor. A roller follower engages the cam and is operatively connected to a compression plate under which at least one compressible conduit containing the patient's blood extends. The stroke volume of blood contained in the conduit can also be controlled.

8 Claims, 7 Drawing Sheets

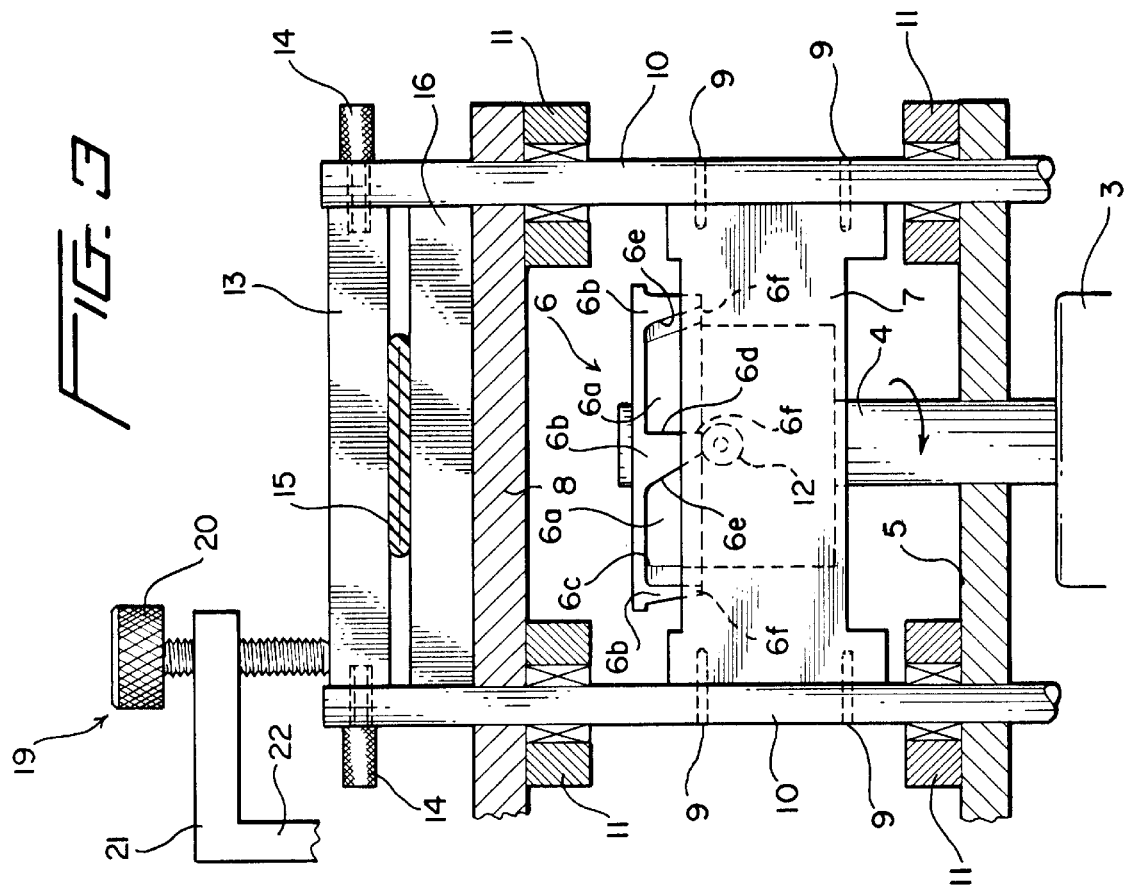
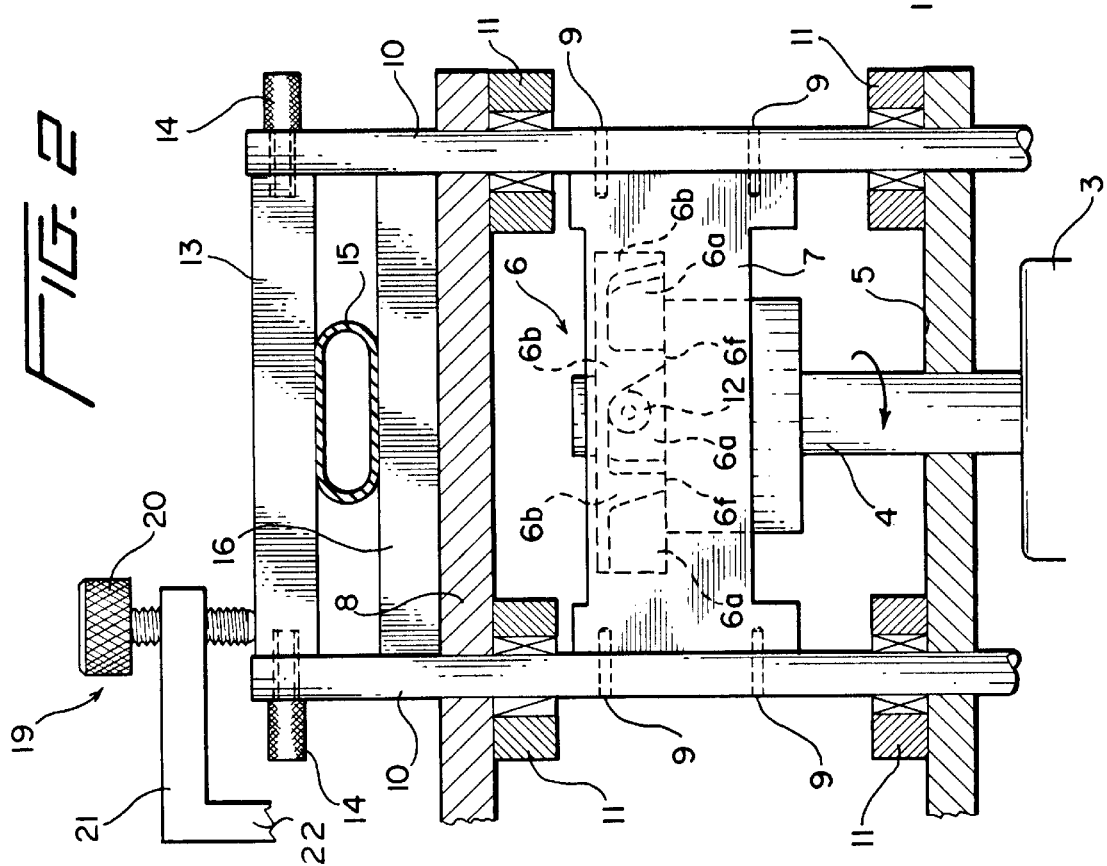

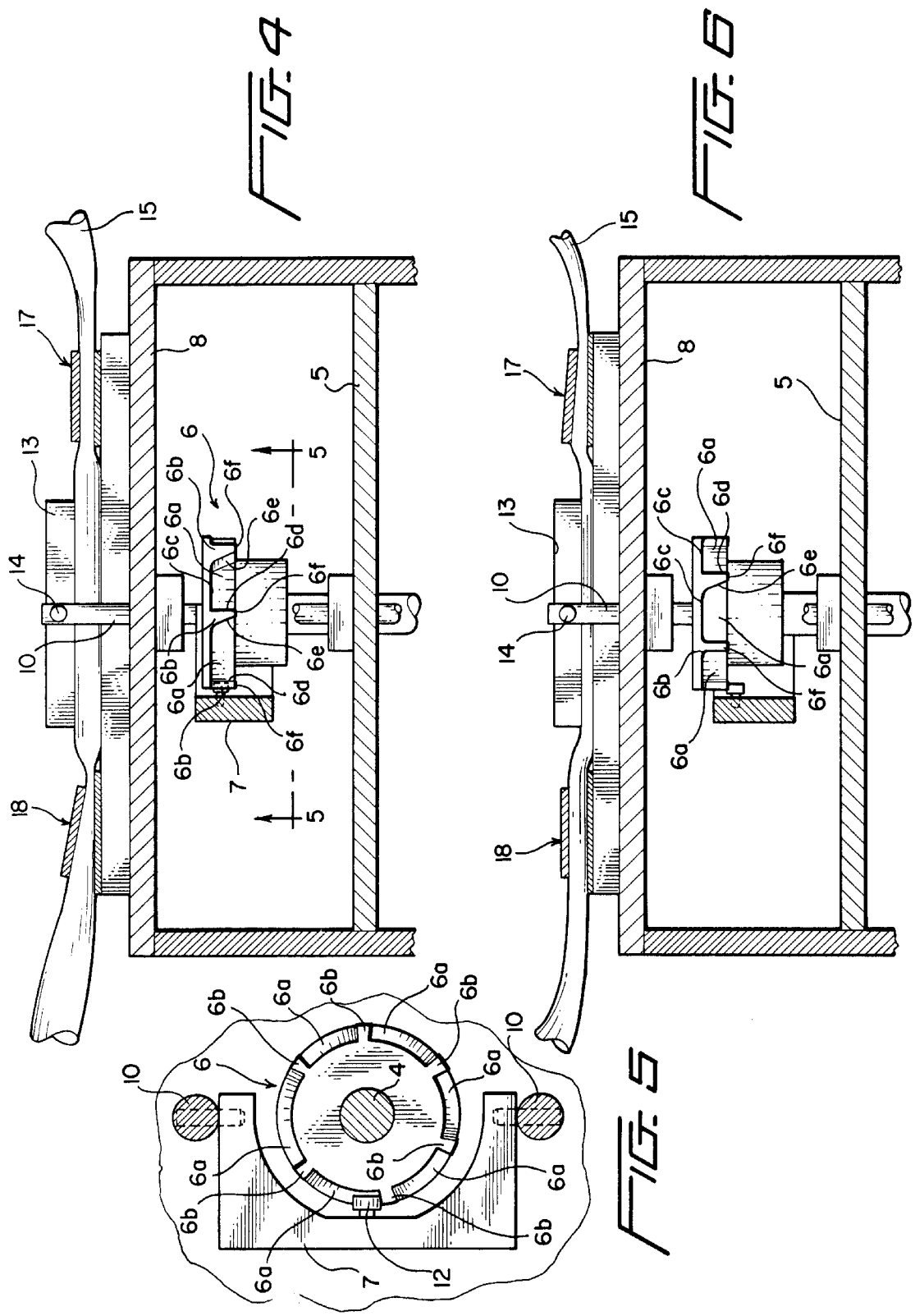

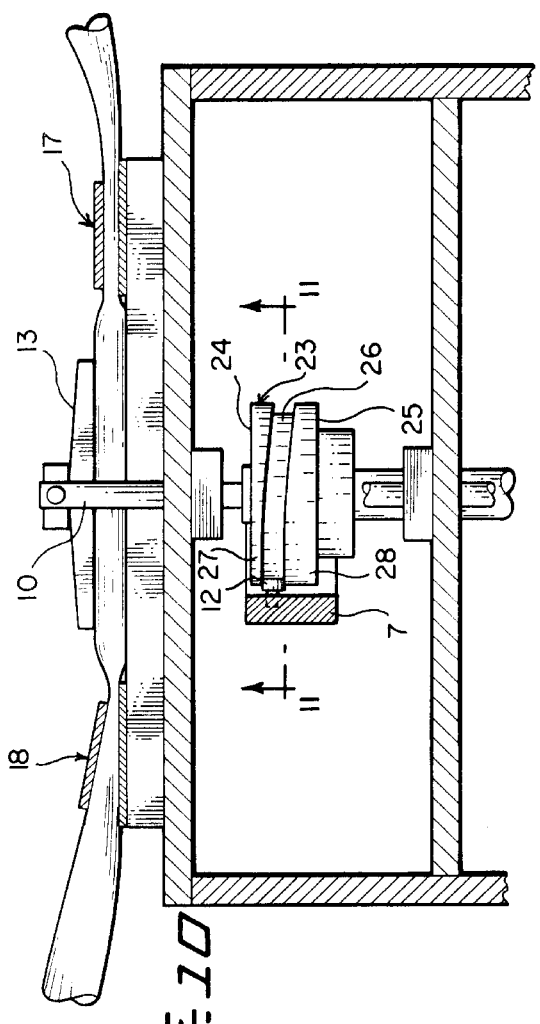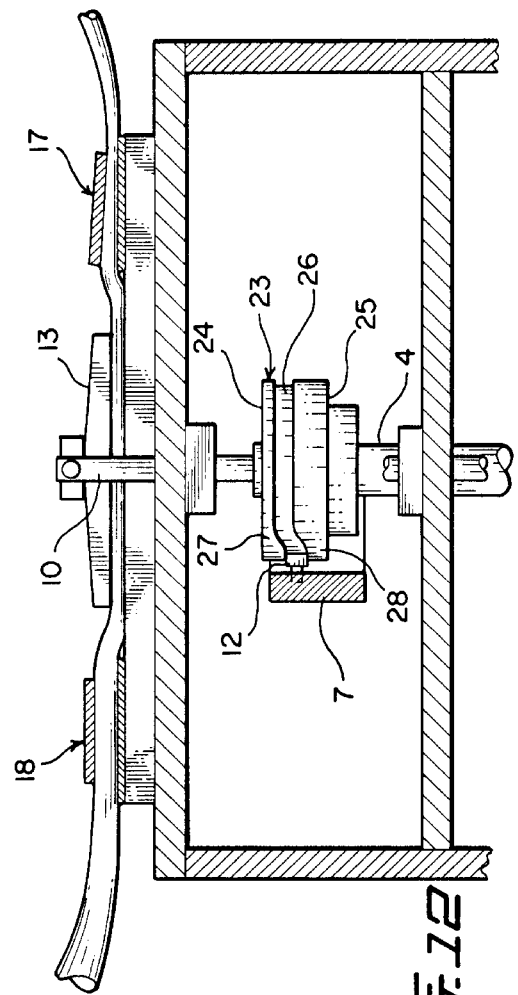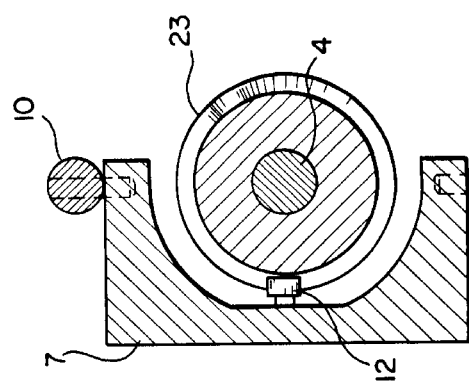

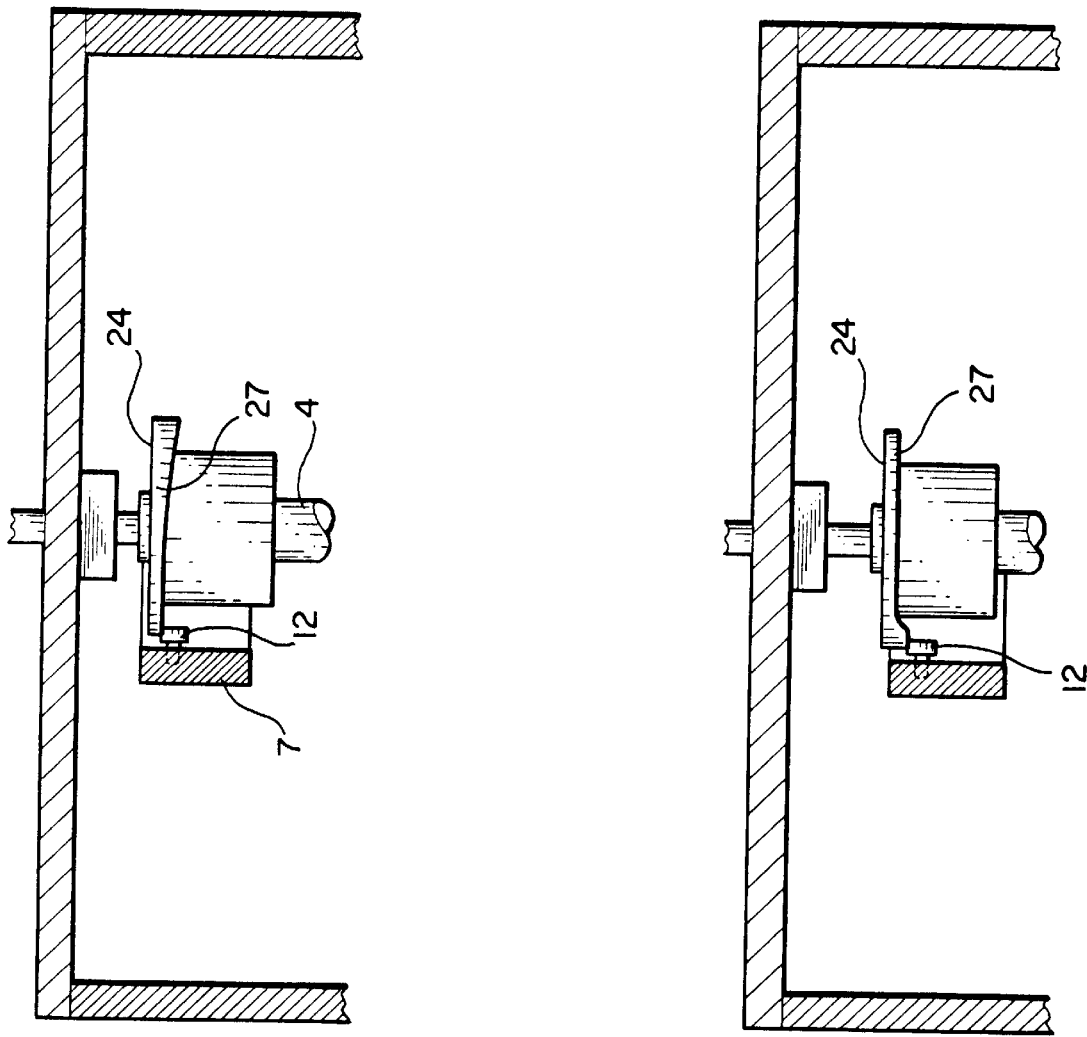

CAM CONTROLLED PULSATILE FLOW PUMP FOR NEONATAL AND BIVENTRICULAR CARDIAC SUPPORT SYSTEMS

BACKGROUND OF THE INVENTION

Pulsatile flow pumps for use in cardiopulmonary bypass procedures have been proposed as disclosed in U.S. Pat. Nos. 4,143,425 dated Mar. 13, 1979 and 4,293,961 dated Oct. 13, 1981. The pumps disclosed in these patents include a blood conveying conduit under a compression plate driven during the systole phase by a flat pawl riding in a helical cam groove provided in a rotor. During diastole, the blood filling the conduit causes the compression plate to return to the initial position preliminary to the systole phase.

While these pumps have been satisfactory for their intended purpose, they have been subject to certain disadvantages in that when using the prior art pumps in the adult size pulsatile total cardiac support, in biventricular mode, as disclosed in pending patent application Ser. No. 08/371,964, filed Jan. 12, 1995, the load causes undesirable friction between the pawl and helical groove thereby affecting the pulsatile characteristics of the pump.

Furthermore, the construction and arrangement of these prior pumps was such that there was no provision for substituting, or retrofitting, one helical grooved rotor for another depending upon the size of the patient, whether an adult or a child.

Also, there was no provision for controlling the stroke volumes of blood contained in the conduit extending underneath the compression plate of the pump.

To overcome the disadvantages experienced in the prior art pulsatile flow pumps, the cam controlled pulsatile flow pump of the present invention has been devised to reduce the friction between the cam and cam follower; cams having various profiles designed to provide the desired pulsatile flow for a particular patient can be selectively installed in the pump, and the stroke volume of blood contained in the conduit extending underneath the compression plate can be controlled.

SUMMARY OF THE INVENTION

The cam controlled pulsatile flow pump of the present invention comprises, essentially, a motor driven cylindrical cam having a predetermined profile provided on its peripheral surface and engaged by a ball bearing supported roller follower mounted on an H-frame connected to the compression plate of the pump under which the blood conveying conduit extends. The profile configuration of the cam is such that the cam follower causes the compression plate to be pulled downwardly against the conduit during the systole phase but allows the compression plate to rise to the initial position during diastole when the blood fills the conduit.

The cams can be selectively secured to the motor drive shaft, and the cam profile for the neonatal support system comprises six, circumferentially spaced, recesses and six circumferentially spaced depending teeth provided on the outer peripheral surface of the cylindrical cam. Each recess is provided with a horizontal top wall and opposite end walls. One end wall extends substantially 85 degrees from the vertical in a direction toward the other end wall, and the other end wall slopes substantially 75 degrees from the vertical in a direction toward the first end wall. The space between one end wall of one recess and the other end wall of the adjacent recess forming a respective depending tooth having a horizontal bottom surface.

The cam profile for the biventricular cardiac support system comprises a cylindrical cam having a top wall and a bottom wall and a circumferentially extending helical recess provided in the peripheral surface thereof. One side of the recess in proximity to the top wall of the cam has a flange portion or shelf adapted to be engaged by the roller follower for actuation of the compression plate during the systole phase. The recess extends horizontally in proximity to the top wall of the cam for approximately 240 degrees and then in a direction toward the bottom wall for approximately 120 degrees. The opposite side of the recess can also be provided with a second shelf adjacent the bottom wall of the cam and adapted to be engaged by the roller follower to force the compression plate upwardly during diastole.

The stroke volume of blood contained in the conduit extending underneath the compression plate can be controlled by an adjustable stop member provided by a set screw positioned above and engageable with the compression plate of the pump. By lowering the set screw the height to which the compression plate can rise during filling (diastole) is reduced. By adjusting the set screw in a direction away from the compression plate, the stroke volume is allowed to increase, by letting the conduit fill more completely.

Pump output is a function of stroke volume X pump rate. The cams described afford a broad spectrum of stroke volumes (from 1.0 ml to 70.0 ml) and a large spectrum of pump rates, from 0 to 150 beats per minute. This means that infants, as small as premature babies of 1.0 kg as well as adults exceeding 200 pounds can be supported by the pump configurations described herein. This versatility of the design has been demonstrated in vitro in the laboratory and in experimental animals.

In addition, physiologic pulsatile flow has been demonstrated. Physiologic pulsatile flow, as produced by the normal human heart, does not result in hypoxia, anaerobic glycolysis, or interstitial fluid accumulation. But steady flow does induce this pathophysiology.

Criteria for physiologic pulsatile flow are as follows, and have been published by the applicants: (1) Physiologic stroke volume, approximately 1.0 ml/kg; (2) Physiologic dP/dT of the upstroke of the arterial pressure trace, no less than 1000 mm/hg per second; (3) Physiologic pulse pressure, no less than 40 mm/hg; (4) Physiologic rate, varying from 140/min in infants to 60/min in adults; (5) Physiologic output, ranging from 150/ml/kg in infants to 80 ml/kg/min in 200 lb adults can be produced with these cams and adjuncts in vitro (up to 7.0 l/min output); and (6) Physiologic ejection time, approximately 415 milli/sec minus 1.5× pump rate, after Weissler. This has been achieved in infant size experimental animals and in adult size animals as well.

BRIEF DESCRIPTION OF THE DRAWINGS

FIG. 2 is an end view partly in section of the pump of FIG. 1 showing the position of the cam, cam follower, compression plate, and set screw mechanism during the inflation of the compressible conduit;

FIG. 3 is an end view similar to FIG. 2 but showing the position of the cam, cam follower, and compression plate during the compression of the conduit;

FIG. 4 is a side elevational view, partly in section, of the pump of FIG. 1 showing the closing of the outlet valve and opening of the inlet valve during the filling of the compressible conduit;

FIG. 5 is a view taken along line 5—5 of FIG. 4;

FIG. 6 is a side elevational view similar to FIG. 4 but showing the opening of the outlet valve and closing of the inlet valve during the compression of the conduit;

FIG. 10 is a side elevational view, partly in section, of the pump of FIG. 8 showing the closing of the outlet valve and opening of the inlet valve during the filling of the compressible conduits;

FIG. 11 is a view taken along line 11—11 of FIG. 10;

FIG. 12 is a side elevational view similar to FIG. 10 but the opening of the outlet valve and closing of the inlet valve during the compression of the conduits;

FIG. 13 is a side elevational view, partly in section, similar to FIG. 10 but showing another embodiment of the cam; and FIG. 14 is a side elevational view similar to FIG. 12 but employing the cam shown in FIG. 13.

DESCRIPTION OF THE PREFERRED EMBODIMENTS

Figure 1:
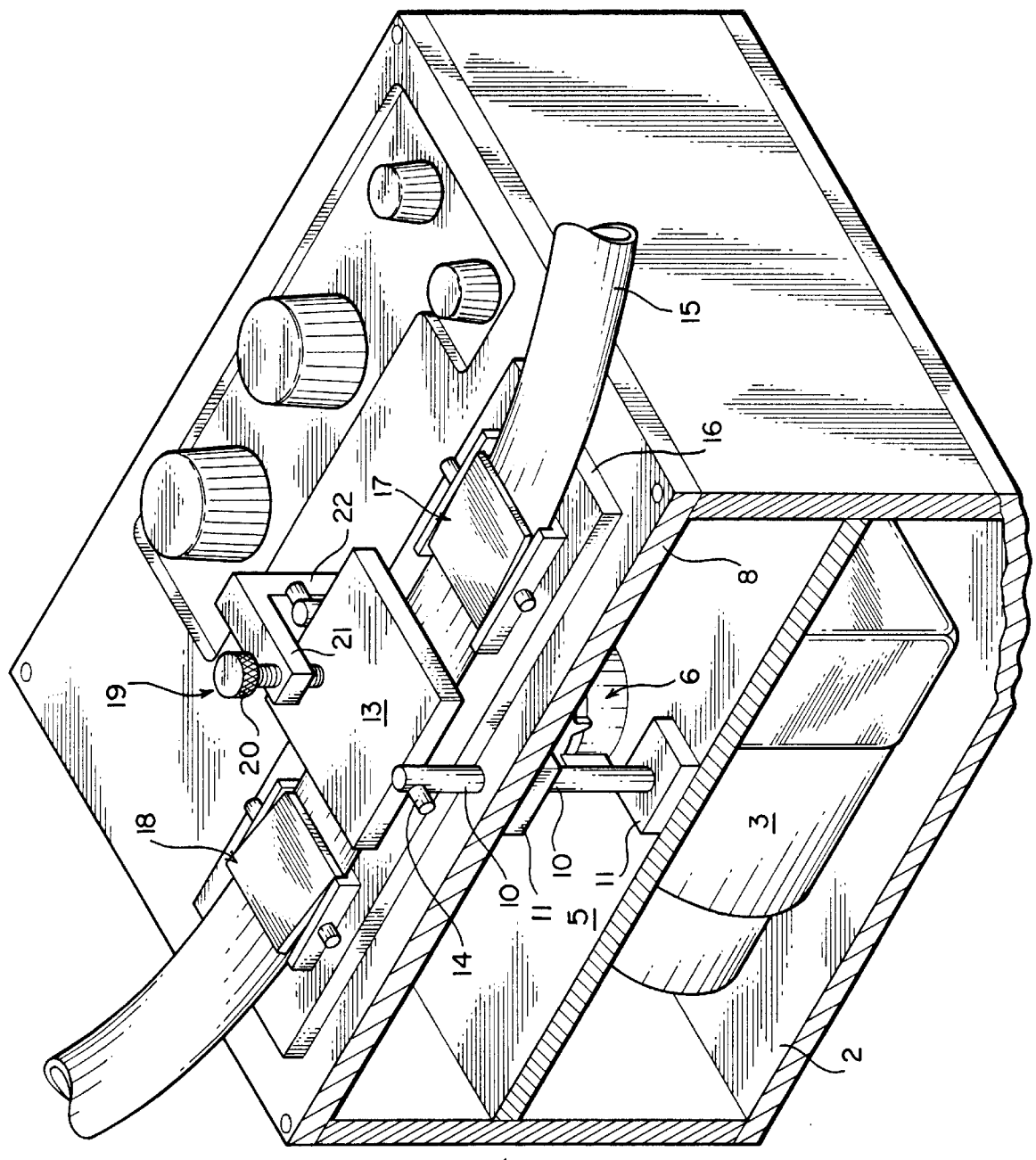
FIG. 1 is a perspective view of a pulsatile flow pump having a cam for a neonatal cardiac support system, and a set screw mechanism for controlling the stroke volume.
Figure 7:
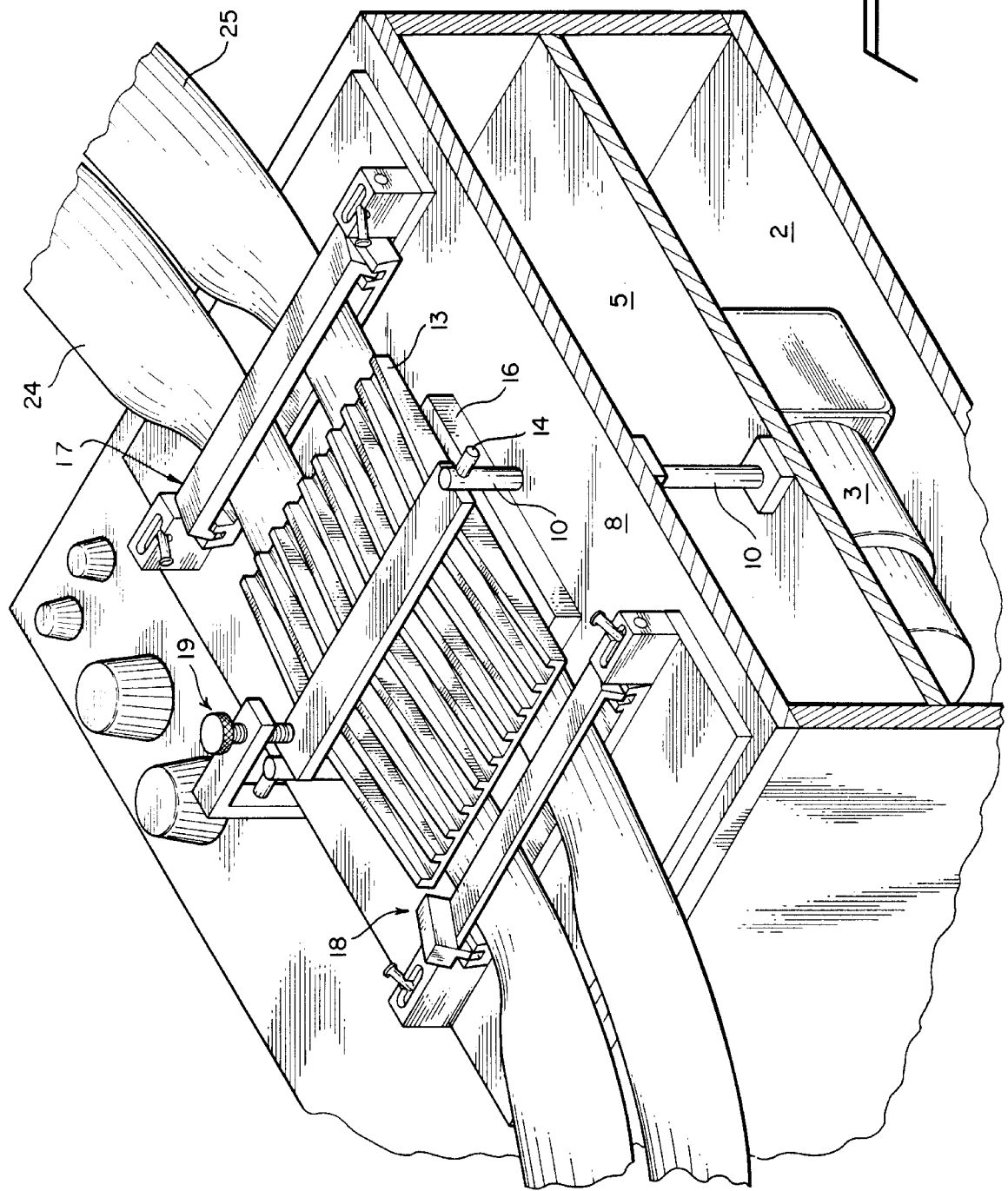
FIG. 7 is a perspective view of the pump employed in a biventricular cardiac support system.
Figure 9:
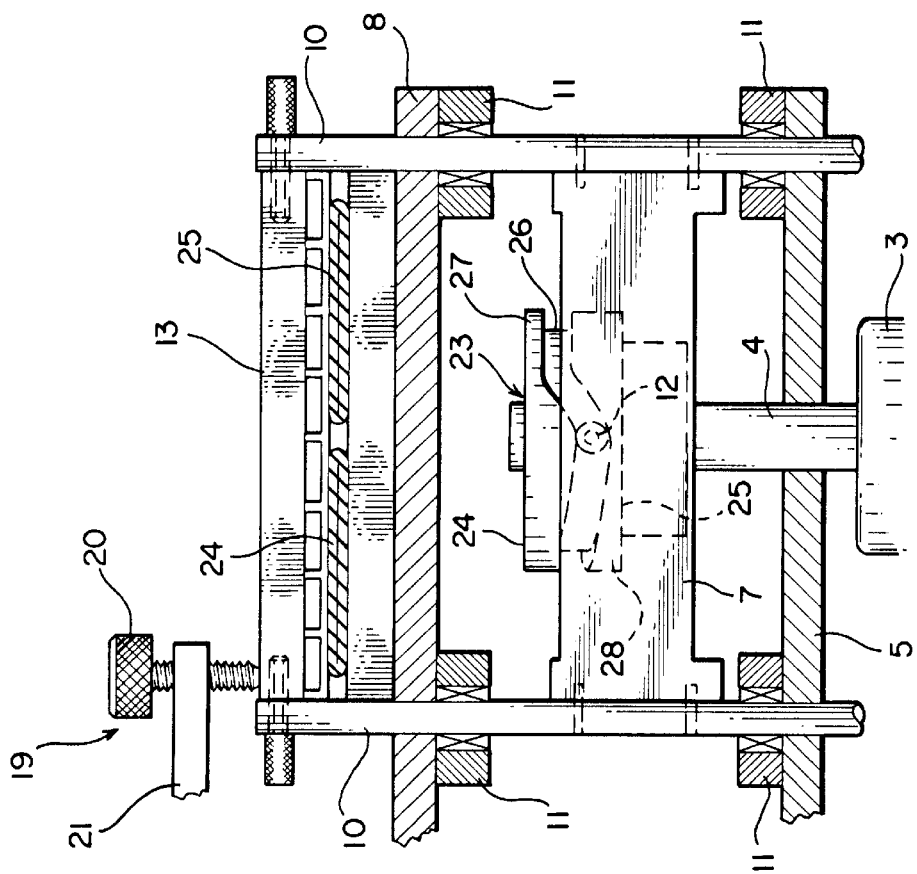
FIG. 9 is an end view similar to FIG. 8 but showing the position of the cam, cam follower, and compression plate during the compression of the conduits.
Figure 8:
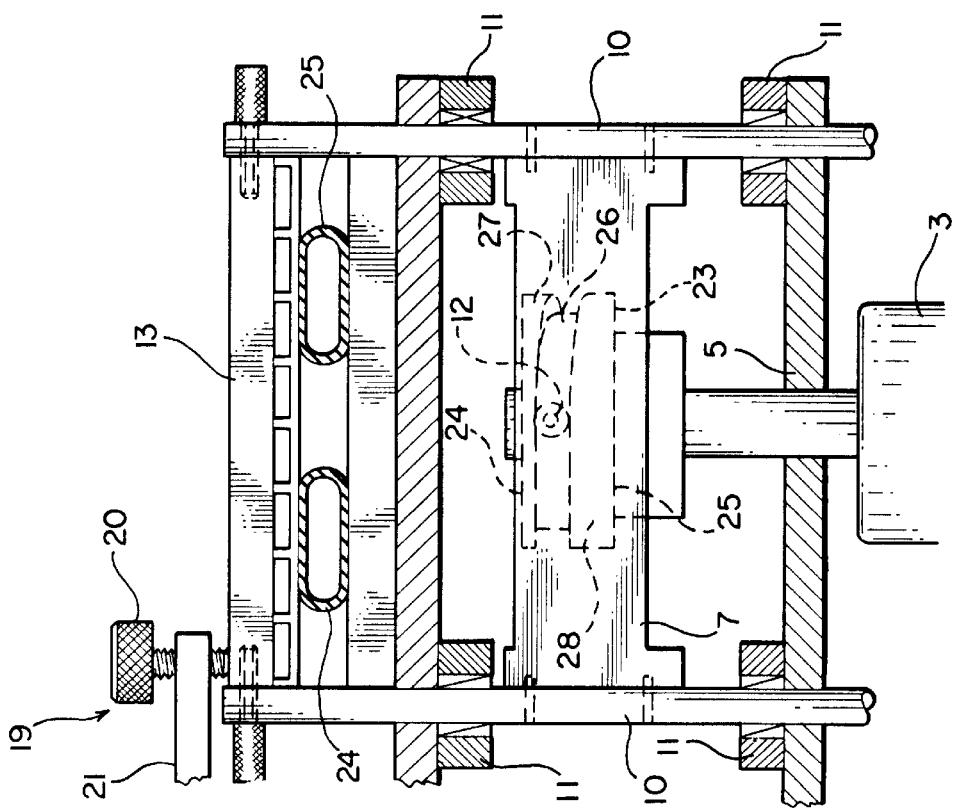
FIG. 8 is an end view partly in section of the pump of FIG. 7 showing one embodiment of the profile and position of the cam, cam follower, compression plate, and screw adjustment mechanism during the inflation of the conduits.

Referring to the drawings and, more particularly to FIGS. 1 to 3, the cam controlled pulsatile flow pump of the present invention comprises a housing 1 having a bottom wall 2 supporting a motor 3 having a driven shaft 4 extending upwardly through a floor 5 in the housing. The shaft 4 has a cylindrical cam 6 detachably connected thereto, to be described more fully hereinafter. A cross-beam 7 is positioned in the housing 1 between the floor 5 and top wall 8 of the housing. The opposite ends of the cross-beam 7 are fastened as at 9 to a pair of spaced, parallel, vertically extending rods 10 slidably mounted in suitable bearings 11 secured to the top surface of the floor 5 and the bottom surface of the top wall 8. A ball bearing supported roller follower 12 is mounted on the cross-beam 7 and engages the profile of the cam 6, and a compression plate 13 is detachably connected to the upper ends of the rods 10 by thumb screws 14. A compressible shunt or conduit 15 for conveying blood through a patient is positioned between the movable compression plate 13 and a fixed plate 16 mounted on the top wall 8 of the housing 1. The conduit 15 is provided with external inlet and outlet plate valves 17 and 18, respectively, of the type disclosed in U.S. Pat. No. 5,383,839 dated Jan. 24, 1995, the disclosure of which is incorporated herein by reference.

The specific profile of the cam 6 is designed for use in a neonatal cardiac support system and, as shown in FIGS. 2 to 6, comprises six, circumferentially spaced, recesses 6a and six, circumferentially spaced depending teeth 6b provided on the outer peripheral surface of the cylindrical cam. Each recess 6a is provided with a horizontal top wall or shelf 6c and opposite end walls 6d and 6e. End wall 6d extends substantially 85 degrees from the vertical in a direction toward end wall 6e which slopes substantially 75 degrees from the vertical in a direction toward end wall 6d. The depending teeth 6b are positioned between the end wall 6d of one recess 6a and the opposite end wall 6e of the adjacent recess 6a, each depending tooth 6b having a horizontal bottom surface 6f, the purpose of which is to maintain peak systolic hold time.

By this construction and arrangement, during the clockwise rotation of the cam 6, as shown in FIGS. 2 and 3, the cam follower 12 will roll on the cam profile resulting in the reciprocatory movement of the compression plate 13. Specifically, during the filling of the conduit 15 with the patient's blood, the diastole phase, the follower 12 will be positioned against the shelf 6c of the cam 6. Continued rotation of the cam 6 will cause the follower 12 to ride on the sloped end wall 6e to the horizontal surface 6f of the tooth 6b resulting in the compression plate 13 being pulled downwardly to compress the conduit 15 to thereby pump the blood therefrom, the systole phase. The ratio of diastole is twice that of systole which is accomplished by allotting 120 degrees of rotation of the cam 6 to systole (pumping phase) and 240 degrees to diastole (filling phase). As will be seen in FIG. 4, during diastole the inlet valve 17 is open and the outlet valve 18 is closed, and during systole the inlet valve is closed and the outlet valve is open.

The cam controlled pulsatile flow pump of the present invention provides physiologic pulsatile flow to improve the wave form within the circulatory system, thereby producing better oxygenation and less interstitial fluid accumulation than afforded by steady flow or nonphysiologic pulsatile flow.

Provision is also made for controlling the stroke volume. To this end, the external plate valves 17 and 18 can be manually positioned farther apart or closer together, and a compression plate 13 of an appropriate length can be connected to the rods 10 by screws 14. By this construction and arrangement, the length of the portion of the conduit 15 containing the blood is varied, thereby increasing or diminishing the stroke volume as desired.

The stroke volume can also be controlled by an adjustable stop member 19, as shown in FIGS. 1 to 3, comprising a set screw 20 threadably mounted in an arm 21 spaced above and extending over the top of the compression plate 13. The arm 21 is integral with a vertical post 22 supported on the top wall 8. By lowering the set screw 20, the height to which the compression plate 13 can rise during filling (diastole) is reduced. Adjusting the screw 20 in the opposite direction to increase the height to which the compression plate 13 can rise during filling will allow the conduit 15 to fill more completely, thereby allowing the stroke volume to increase.

While the cam controlled pulsatile flow pump shown in FIGS. 1 to 6 has been described for use in a neonatal cardiac support system, FIGS. 7 to 12 illustrate the cam controlled pump for use in a biventricular cardiac support system. In this arrangement, the cam 6, is removed from the motor shaft 4 and a cylindrical cam 23 having a desired profile configuration is mounted on the shaft 4 by a suitable set screw (not shown). A pair of conduits 24 and 25 extend through the inlet valve 17, under the compression plate 13, and through the outlet valve 18, the conduits being connected to the patient's heart, as disclosed in the aforementioned pending application Ser. No. 08/371,964 filed Jan. 12, 1995.

The cam 23 comprises a cylindrical cam having a top wall 23a and a bottom wall 23b and a circumferentially extending helical recess 26 provided in the peripheral surface of the cam. One side of the recess 26 in proximity to the top wall 24 of the cam has a flange portion or shelf 27 adapted to be engaged by the roller follower 12 for actuation of the compression plate 13 during the systole phase. The recess 26 extends horizontally in proximity to the top wall 23a of the cam 23 for approximately 240 degrees of the cam rotation and then in a direction toward the bottom 23b of the cam for approximately 120 degrees of cam rotation. The opposite side of the recess is also provided with a shelf 28 which is engaged by the follower 12, whereby the rotation of the cam 23 will cause the follower 12 and associated cross-beam 7 and rods 10 to push the compression plate 13 upwardly to expand the conduits to the fill position. In this arrangement, the upper surfaces of the conduits 24, 25 are fixedly attached, as by gluing, to the bottom surface of the compression plate 13, whereby the positive forcing of the compression plate upwardly will cause blood to be drawn into the conduits by induction of negative pressure.

In situations where it is not desired to force the filling of the conduits 24 and 25 during diastole, the lower shelf 23b is eliminated, as shown in FIGS. 13 and 14, so that the gradual expansion of the conduits 24 and 25 with filling will occur without induction of negative pressure, and the stroke volume will vary from beat to beat, depending upon filing pressure; that is, the pressure in the patient's right or left atrium.

From the above description, it will be appreciated by those skilled in the art that the cam controlled pulsatile flow pump of the present invention is an improvement on heretofore employed pulsatile flow pumps, in that cams having various profiles designed to provide the desired pulsatile flow for a particular patient can be selectively installed in the pump. The bearing supported roller follower 12 reduces the friction between the cam and follower, and the stroke volume of blood contained in the conduit extending underneath the compression plate 13 can be controlled.

It is to be understood that the form of the invention herewith shown and described is to be taken as a preferred example of the same, and that various changes in the shape, size, and arrangement of parts may be resorted to, without departing from, the spirit of the invention or scope of the subjoined claims.

We claim:

1. A cam controlled pulsatile flow pump comprising a motor having a rotary output shaft, a cylindrical cam, said cam being connected to said shaft, a selected cam profile provided on the peripheral surface of said cam, a roller follower engaging said cam profile, said roller follower being mounted on a cross-beam, opposite ends of said cross-beam being connected to a pair of spaced parallel vertically extending rods, a compression plate positioned between the upper end portions of said rods, means for detachably connecting the compression plate to the upper end portions of said rods, a fixed plate positioned below and spaced from the compression plate, at least one compressible conduit containing fluid extending between the fixed plate and compression plate and adapted to be engaged by the compression plate, whereby rotation of the cam causes the roller follower and associated cross-beam and vertically extending rods to impart vertical reciprocation to the compression plate, whereby fluid is pumped through the compressible conduit and an adjustable stop member positioned over the compression plate to thereby limit the upward movement of the compression plate, whereby the stroke volume of fluid in the conduit may be controlled.

2. A cam controlled pulsatile flow pump according to claim 1, wherein the adjustable stop member comprises an arm spaced above and extending over the top surface of said compression plate, and a set screw threadably mounted in the arm adapted to be engaged by the top surface of the compression plate.

3. A cam controlled pulsatile flow pump comprising a motor having a rotary output shaft, a cylindrical cam, said cam being connected to said shaft, a selected cam profile provided on the peripheral surface of said cam, a roller follower engaging said cam profile, said roller follower being mounted on a cross-beam, opposite ends of said cross-beam being connected to a pair of spaced parallel vertically extending rods, a compression plate positioned between the upper end portions of said rods, means for detachably connecting the compression plate to the upper end portions of said rods, a fixed plate positioned below and spaced from the compression plate, at least one compressible conduit containing fluid extending between the fixed plate and compression plate, and adapted to be engaged by the compression plate, whereby rotation of the cam causes the roller follower and associated cross-beam and vertically extending rods to impart vertical reciprocation to the compression plate, whereby fluid is pumped through the compressible conduit, an external inlet plate valve positioned in proximity to one end of the compression plate, and an external outlet plate valve positioned in proximity to the opposite end of the compression plate, the conduit extending through said inlet and outlet valves, whereby the stroke volume of fluid in the conduit may be controlled by manually positioning the plate valves farther apart or closer together, and connecting a compression plate of an appropriate length to the vertical rods, to thereby vary the length of the portion of the conduit containing the fluid.

4. A cam controlled pulsatile flow pump according to claim 3, wherein the pump is employed in a neonatal cardiac support system, the cam profile comprising six circumferentially spaced recesses and six circumferentially spaced depending teeth provided on the outer peripheral surface of the cylindrical cam, each recess having a horizontal top wall and opposite end walls, one end wall extending substantially 85 degrees from the vertical in a direction toward the other end wall, said other end wall sloping substantially 75 degrees from the vertical in a direction toward the first mentioned end wall, the space between one end wall of one recess and the other end wall of the adjacent recess forming a respective depending tooth having a horizontal bottom surface, whereby during diastole the follower is positioned against the top wall of the cam recess, and during systole the follower is positioned on the horizontal bottom surface of said depending tooth, systole being accomplished during 120 degrees rotation of said cam and diastole being accomplished during 240 degrees rotation of said cam, six systolic intervals totaling 120 degrees and six intervening diastolic intervals totaling 240 degrees, per cam rotation.

5. A cam controlled pulsatile flow pump according to claim 3, wherein the pump is employed in a biventricular cardiac support system, a pair of compressible conduits extending through said plate valves and underneath said compression plate, the cylindrical cam being vertically oriented and having a top wall and a bottom wall, a circumferentially extending helical recess provided in the peripheral surface of the cam, one side of the recess in proximity to the top wall of the cam having a shelf engaged by the roller follower for actuation of the compression plate during systole, said recess extending horizontally in proximity to the top wall of the cam for approximately 240 degrees rotation of said cam and then in a direction toward the bottom wall of the cam for approximately 120 degrees of cam rotation, whereby during systole the downward movement of the compression plate compresses the conduits to pump the blood therefrom, and during diastole the upward movement of the compression plate is caused by the pressure of the blood flowing into the conduits and the resultant expansion thereof.

6. A cam controlled pulsatile flow pump according to claim 4, wherein a second shelf is provided on the opposite side of the recess from said first mentioned side, said roller follower engaging said second shelf, the upper surfaces of said conduits being fastened to the lower surface of said compression plate, whereby rotation of the cam causes the follower and associated cross-beam and rods to push the compression plate upwardly to expand the conduits causing blood to be drawn into the conduits by induction.

7. A cam controlled pulsatile flow pump for cardiac support systems comprising a motor having a rotary output shaft, cam means connected to said shaft, said cam means having a selected cam profile, a follower engaging said cam profile, a compression plate operatively connected to said cam follower, a fixed plate positioned below and spaced from the compression plate, at least one compressible conduit containing fluid extending between the fixed plate and compression plate, and adapted to be engaged by the compression plate, whereby rotation of the cam means causes the follower to impart vertical reciprocation to the compression plate, to thereby pump fluid through the compressible conduit, said compression plate having a selected length, thereby determining the length of the portion of the conduit containing the fluid, said conduit having a selected diameter, an adjustable stop member positioned over the compression plate to limit the upward movement of the compression plate, to thereby control the stroke volume of fluid in the conduit, an external inlet valve positioned in proximity to one end of the compression plate, an external outlet valve positioned in proximity to the opposite end of the compression plate, said valves being manually positioned farther apart or closer together, to thereby control the stroke volume of fluid in the conduit, whereby physiologic pulsatile flow is provided requiring physiologic stroke volume, physiologic dP/dT of upstroke of the arterial pressure trace, physiologic pulse pressure, physiologic rate, physiologic pump output per minute and physiologic ejection time, to thereby provide physiologic pulsatile flow for patients of various sizes from 1.0 kg to 100 kg, with stroke volumes from 1.0 ml to 70.0 ml and pump outputs as high as 7.0 liters per minute.

8. A cam controlled pulsatile flow pump selectively employed in a neonatal cardiac support system for a child patient or a biventricular cardiac support system for an adult patient, comprising a motor having a rotary output shaft, a cylindrical cam, said cam having a selected cam profile on the peripheral surface thereof for controlling the pulsatile flow, said selected cam profile being selected from the group consisting of a child patient profile or an adult patient profile, means for detachably connecting a selected cam to said shaft, a roller follower engaging said cam profile, said roller follower being mounted on a cross-beam, opposite ends of said cross-beam being connected to a pair of spaced parallel vertically extending rods, a compression plate positioned between the upper end portions of said rods, means for detachably connecting the compression plate to the upper end portions of said rods, a fixed plate positioned below and spaced from the compression plate, at least one compressible conduit containing fluid extending between the fixed plate and compression plate and adapted to be engaged by the compression plate, whereby rotation of the cam causes the roller follower and associated cross-beam and vertically extending rods to impart vertical reciprocation to the compression plate, whereby fluid is pumped through the compressible conduit.

\* \* \* \* \*